United States Patent [19]

Gericke et al.

[11] Patent Number: 5,130,322
[45] Date of Patent: Jul. 14, 1992

[54] CHROMAN DERIVATIVES

[76] Inventors: Rolf Gericke; Manfred Baumgarth; Ingeborg Lues; Rolf Bergmann; Jacques De Peyer, c/o E. Merck Postfach 4119, D-6100 Darmstadt, Fed. Rep. of Germany

[21] Appl. No.: 562,542

[22] Filed: Aug. 3, 1990

[30] Foreign Application Priority Data

Aug. 5, 1989 [DE] Fed. Rep. of Germany ....... 3826001

[51] Int. Cl.$^5$ .................... A61K 31/44; C07D 401/04
[52] U.S. Cl. .................... 514/337; 514/253; 514/274; 514/256; 514/422; 514/456; 546/269; 544/238; 544/333; 544/405; 548/525; 549/401
[58] Field of Search .................... 546/269; 514/337

[56] References Cited

U.S. PATENT DOCUMENTS

| | | | |
|---|---|---|---|
| 4,446,113 | 5/1984 | Evans et al. | 422/267 |
| 4,542,149 | 9/1985 | Evans et al. | 514/422 |
| 4,640,928 | 2/1987 | Willcocks | 514/422 |
| 4,644,070 | 2/1987 | Evans et al. | 549/399 |
| 4,772,603 | 9/1988 | Evans | 514/241 |
| 4,786,639 | 11/1988 | Evans | 514/254 |
| 4,971,982 | 11/1990 | Attwood et al. | 514/456 |

FOREIGN PATENT DOCUMENTS

296975 12/1988 European Pat. Off. .

OTHER PUBLICATIONS

Rolf Gericke et al., CA 113:152203h CA112:216696k.

Bergmann et al., CA 112:55531K.
Blarer CA111:7227y.

*Primary Examiner*—Jane T. Fan
*Attorney, Agent, or Firm*—Millen, White & Zelano

[57] ABSTRACT

The invention relates to chroman derivatives of the formula I

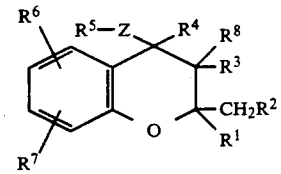

in which
 $R^1$ is A,
 $R^2$ is OA,
 $R^3$ is OH,
 $R^4$ is H, or
 $R^3$ and $R^4$ together are a bond,
 $R^5$ is a 2-oxo-1,2-dihydro-1-pyridyl or 2-oxo-2,3-dihydro-4-pyrodyl radical which is optionally monosubstituted by A,
 $R^6$ is CN,
 $R^7$ and $R^8$ are each H,
 Z is O, NH or a bond, and
 A is alkyl having 1-6 C atoms,
or a physiologically acceptable salt thereof.

10 Claims, No Drawings

CHROMAN DERIVATIVES

SUMMARY OF THE INVENTION

The invention relates to novel chroman derivatives of the formula I

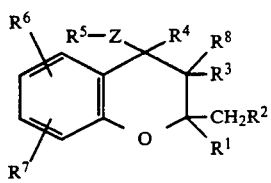

in which
R' is H or A,
$R^2$ is F, Cl, Br, I, OH, OA, OAc, SA, $NO_2$, $NH_2$, NHA, $NA_2$, CN or COOA,
$R^3$ is H, OH, OA or OAc,
$R^4$ is H,
$R^3$ and $R^4$ together are also a bond,
$R^5$ is a pyridyl, pyridazinyl, pyrimidinyl, pyrazinyl, oxodihydropyridyl, oxodihydropyridazinyl, oxodihydropyrimidinyl, oxodihydropyrazinyl, 2-pyrrolidinon-1-yl or 3-oxocyclopenten1-yl radical which is unsubstituted, monosubstituted or disubstituted by A, F, Cl, Br, I, OH, OA, OAc, SH, $NO_2$, $NH_2$, NHAc, COOH and/or COOA,
$R^6$ and $R^7$ are each H, A, HO, AO, CHO, ACO, ACS, HOOC, AOOC, AO-CS, ACOO, A-CS-O, hydroxyalkyl, mercaptoalkyl, $NO_2$, $NH_2$, NHA, $NA_2$, CN, F, Cl, Br, I, $CF_3$, ASO, $ASO_2$, AO-SO, $AO-SO_2$, AcNH, AO-CO-NH, $H_2NSO$, HANSO, $A_2NSO$, $H_2NSO_2$, $HANSO_2$, $A_2NSO_2$, $H_2NCO$, HANCO, $A_2NCO$, $H_2NCS$, HANCS, $A_2NCS$, ASONH, $ASO_2NH$, AOSONH, $AOSO_2NH$, ACO-alkyl, nitroalkyl, cyanoalkyl, A—C(=NOH) or A—C(=$NNH_2$),
$R^8$ is H or A,
Z is O, S, NH or a bond,
A is alkyl having 1-6 C atoms,
-alkyl is alkylene having 1-6 C atoms and
Ac is alkanoyl having 1-8 C atoms or aroyl having 7-11 C atoms
and their salts.

The invention was based on the object of finding novel compounds having useful properties, in particular those which can be used for the preparation of medicaments.

It has been found that the compounds of the formula I and their physiologically acceptable salts possess, combined with good tolerability, useful pharmacological properties. Thus, they show effects on the cardiovascular system, it usually being possible to observe a selective effect on the coronary system at lower doses and a hypotensive effect at higher doses. In the coronary system, for example, decreases in resistance and increases in flow occur, the influence on the heart rate remaining low. Furthermore, the compounds show a relaxant effect on various smooth muscle organs (gastrointestinal tract, respiratory system and uterus). The effects of the compounds can be determined with the aid of methods which are known per se, as are given, for example, in EP-A1-76,075, EP-A1-l73,848 or AU-A-45,547/85 (Derwent Farmdoc No. 86081769) and by K.S. Meesmann et al., Arzneimittelforschung 25 (11), 1975, 1770-1776. Suitable experimental animals are, for example, mice, rats, guinea pigs, dogs, cats, apes or pigs.

The compounds can therefore be used as active medicament compounds in human and veterinary medicine. In addition, they can be used as intermediates for the preparation of further active medicament compounds.

In the formulae given, A is a preferably an unbranched alkyl group having 1-6, preferably 1-4, in particular 1, 2 or 3 C atoms, in detail preferably methyl, in addition preferably ethyl, propyl, isopropyl, butyl, isobutyl, and furthermore preferably sec.-butyl, tert.-butyl, pentyl, isopentyl (3-methylbutyl), hexyl or isohexyl (4-methylpentyl).

The group "—alkyl" preferably stands for —$CH_2$— or —$CH_2CH_2$—.

Ac is preferably alkanoyl having 1-6, in particular 1, 2, 3 or 4 C atoms, in detail preferably formyl or acetyl, furthermore preferably propionyl, butyryl, isobutyryl, pentanoyl or hexanoyl, and in addition preferably benzoyl, o-, m- or p-toluyl, 1- or 2-naphthoyl.

$R^1$ is preferably A, in particular methyl or ethyl, preferably methyl.

$R^2$ is preferably OA, in particular methoxy or ethoxy; furthermore $R^2$ is preferably OH.

If $R^4$ is H, $R^3$ is preferably OH, and in addition preferably O—CHO or O—$COCH_3$.

Z is preferably O or a bond.

The group $R^5$—Z is preferably 1,2-dihydro-2-oxo-1-pyridyl, furthermore 2-hydroxy-4-pyridyloxy (=1,2-dihydro-2-oxo-4-pyridyloxy), 6-hydroxy-3-pyridazinyloxy (=1,6-dihydro-6-oxo-3-pyridazinyloxy), 2-,3- or 4-pyridyloxy, 1,6-dihydro-3-hydroxy-6-pyridazinon-1-yl,1,2-dihydro-4-hydroxy-2-oxo-1-pyridyl, 1,6-dihydro-1-methyl-6-oxo-3-pyridazinyloxy, 1,6-dihydro-1-ethyl-6-oxo-3-pyridazinyloxy, 2-pyrrolidinon-1-yl or 3-oxo-1-cyclopentenyloxy.

In $R^6$ and $R^7$, the following are preferably:
A:methyl, and in addition ethyl;
AO:methoxy, and in addition ethoxy;
ACO:acetyl, and in addition propionyl;
ACS:thioacetyl, and in addition thiopropionyl;
AOOC:methoxycarbonyl, and in addition ethoxycarbonyl;
AO—CS:methoxythiocarbonyl, and in addition ethoxythiocarbonyl;
ACOO:acetoxy, and in addition propionoxy;
ACSO:thio(no)acetoxy, and in addition thio(no)propionoxy;
hydroxyalkyl:hydroxymethyl or 1- or 2-hydroxyethyl;
mercaptoalkyl:mercaptomethyl or 1- or 2-mercaptoethyl;
NHA:methylamino, and in addition ethylamino;
$NA_2$:dimethylamino, and in addition diethylamino;
ASO:methylsulfinyl, and in addition ethylsulfinyl;
$ASO_2$:methylsulfonyl, and in addition ethylsulfonyl;
AO—SO:methoxysulfinyl, and in addition ethoxysulfinyl;
AO—$SO_2$:methoxysulfonyl, and in addition ethoxysulfonyl;
Ac—NH:acetamido, and in addition formamido, propionamido or benzamido;
AO—CO—NH:methoxycarbonylamino, and in addition ethoxycarbonylamino;
HANSO:methylaminosulfinyl, and in addition ethylaminosulfinyl;

A$_2$NSO:dimethylaminosulfinyl, and in addition diethylaminosulfinyl;
HANSO$_2$:methylaminosulfonyl, and in addition ethylaminosulfonyl;
A$_2$NSO$_2$:dimethylaminosulfonyl, and in addition diethylaminosulfonyl;
HANCO:N-methylcarbamoyl, and in addition N-ethylcarbamoyl;
A$_2$NOC:N,N-dimethylcarbamoyl, and in addition N,N-diethylcarbamoyl;
HANCS:N-methylthiocarbamoyl, and in addition N-ethylthiocarbamoyl;
A$_2$NCS:N,N-dimethylthiocarbamoyl, and in addition N,N-diethylthiocarbamoyl;
ASONH:methylsulfinylamino, and in addition ethylsulfinylamino;
ASO$_2$NH:methylsulfonylamino, and in addition ethylsulfonylamino;
AOSONH:methoxysulfinylamino, and in addition ethoxysulfinylamino;
AOSO$_2$NH:methoxysulfonylamino, and in addition ethoxysulfonylamino;
ACO-alkyl:2-oxopropyl, 2-oxobutyl, 3-oxobutyl, 3-oxopentyl;
Nitroalkyl:nitromethyl, 1- or 2-nitroethyl;
Cyanoalkyl:cyanomethyl, 1- or 2-cyanoethyl;
A—C(=NOH):1-oximinoethyl, and in addition 1-oximinopropyl;
A—C(=NNH$_2$):1-hydrazinoethyl, and in addition 1-hydrazinopropyl.

The radicals $R^6$ and $R^7$ are preferably in the 6-and 7-position of the chroman system. However, they may also be in the 5- and 6-, 5- and 7-, 5- and 8-, 6- and 8-and 7- and 8-position.

One of the radicals $R^6$ and $R^6$ is preferably H, whereas the other is different from H. This other radical is preferably in the 6-position, but also in the 5-, 7-or 8-position, and is preferably CN or NO$_2$, in addition preferably CHO, ACO (in particular acetyl), AOOC (in particular methoxycarbonyl or ethoxycarbonyl), ACOO (in particular acetoxy), and furthermore preferably F, Cl, Br, I, CF$_3$, H$_2$NCO, H$_2$NCS or NH$_2$.

The radical $R^8$ is preferably H, and furthermore preferably methyl or ethyl.

Accordingly, the invention in particular relates to those compounds of the formula I in which at least one of the radicals mentioned has one of the previously mentioned preferred meanings. Some preferred groups of compounds can be expressed by the formulae Ia to Ii below, which correspond to the formula I and in which the radicals not designated in more detail have the meaning indicated in the formula I, in which however
in Ia
  $R^1$ is A and
  $R^2$ is OA;
in Ib
  $R^1$ is CH$_3$ and
  $R^2$ is OA;
in Ic
  $R^1$ is CH$_3$ and
  $R^2$ is OCH$_3$;
in Id
  $R^5$—Z is 1,2-dihydro-2-oxo-1-pyridyl,2-hydroxy4-pyridyloxy, 6-hydroxy-3-pyridazinyloxy, 1,6-dihydro-1-methyl-6-oxo-3-pyridazinyloxy, 2-pyrrolidinon-1-yl or 3-oxo-cyclopenten-1-yl-oxy;
in Ie
  $R^5$—Z is 2-pyrrolidinon-1-yl;
in If
  $R^5$—Z is 1,2-dihydro-2-oxo-1-pyridyl;
in Ig
  $R^1$ is CH$_3$,
  $R^2$ is OCH$_3$,
  $R^5$—Z 1,2-dihydro-2-oxo-1-pyridyl,2-hydroxy4-pyridyloxy, 6-hydroxy-3-pyridazinyl-oxy, 1,6-dihydro-1-methyl-6-oxo-3-pyridazinyloxy, 2-pyrrolidinon-1-yl or 3-oxo-cyclopenten-1-yl-oxy and
  $R^8$ is H or CH$_3$;
in Ih
  $R^1$ is CH$_3$,
  $R^2$ is OCH$_3$,
  $R^5$—Z is 2-pyrrolidinon-1-yl and
  $R^8$ is H or CH$_3$;
in Ii
  $R^1$ is CH$_3$,
  $R^2$ is OCH$_3$,
  $R^5$—Z is 1,2-dihydro-2-oxo-1-pyridyl and
  $R^8$ is H or CH$_3$.

Compounds of the formulae I' and Ia' to Ii' are furthermore preferred which correspond to the formulae I and Ia to Ii, but in which in each case additionally $R^3$ is H, OH, OCHO or OCOCH$_3$ and $R^4$ is H, in particular those compounds of the formulae I' and Ia' to Ii' in which in each case additionally $R^3$ is OH and $R^4$ is H.

Compounds of the formulae I'' and Ia'' to Ii'' are furthermore preferred which correspond to the formulae I, and Ia to Ii, but in which in each case $R^3$ and $R^4$ together are additionally a bond.

Compounds of the formulae I, I', I'', Ia to Ii, Ia' to Ii' and Ia'' to Ii'' are in addition preferred, in which in each case additionally
(a)
  $R^6$ is different from H and
  $R^7$ is H;
(b)
  $R^6$ is different from H and is in the 6-position and
  $R^7$ is H;
(c)
  $R^6$ is NO$_2$, CN, CHO, ACO, HOOC, AOOC, ACOO, F, Cl, Br, I, CF$_3$, H$_2$NCO, H$_2$NCS or NH$_2$ and
  $R^7$ is H;
(d)
  $R^6$ is NO$_2$, CN, CHO, ACO, HOOC, AOOC, ACOO, F, Cl, Br, I, CF$_3$, H$_2$NCO, H$_2$NCS or NH$_2$ and is in the 6-position and
  $R^7$ is H;
(e)
  $R^6$ is NO$_2$, CN, CHO, CH$_3$CO, CH$_3$OOC, C$_2$H$_5$OOC or CH$_3$COO and
  $R^7$ is H;
(f)
  $R^6$ is NO$_2$, CN, CHO, CH$_3$CO, CH$_3$OOC, C$_2$H$_5$OOC or CH$_3$COO and is in the 6-position and
  $R^7$ is H;
(g)
  $R^6$ is NO$_2$ or CN and
  $R^7$ is H;
(h)
  $R^6$ is NO$_2$ or CN and is in the 6-position and
  $R^7$ is H;
(i)
  $R^6$ is CN and
  $R^7$ is H;
(j)
  $R^6$ is CN and is in the 6-position and
  $R^7$ is H.

Otherwise, the radicals $R^1$ to $R^8$, Z, A, "-alkyl" and Ac above and below have the meanings given in formula I, if not expressly stated otherwise.

The invention in addition relates to a process for the preparation of chroman derivatives of the formula I, characterized in that a chroman of the formula II

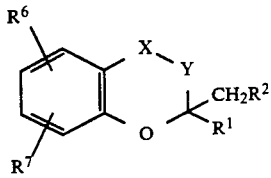

in which
X—Y is

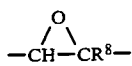

or —CHE—$CR^3R^8$— and
E is Cl, Br, I or a reactively esterified OH group and
$R^1$, $R^2$,
$R^3$, $R^6$,
$R^7$ and $R^8$ have the meanings given in formula I,
is reacted with a compound of the formula III $R^5$—Z—H     III in which
$R^5$ and Z have the meanings indicated in the formula I, or in that in order to prepare a compound of the formula I, in which $R^2$ is OH or $NH_2$, a compound otherwise corresponding to the formula I, but which carries, instead of $R^2$, a group —$OR^9$ or —$NHR^9$, in which $R^9$ is a protecting group which can be removed by hydrogenolysis or solvolysis, is treated with a hydrogenolyzing or solvolyzing agent, and/or in that a compound of the formula I, in which $R^3$ is OH and $R^4$ is H, is dehydrated and/or in that in a compound of the formula I, one or more of the radicals $R^2$, $R^3$, $R^5$, $R^6$ and/or $R^7$ are converted into other radicals $R^2$, $R^3$, $R^5$, $R^6$ and/or $R^7$ and/or in that a basic compound of the formula I is converted into one of its acid addition salts by treating with an acid.

The compounds of the formula I are otherwise prepared by methods which are known per se, as are described in the literature (for example in the standard works such as Houben-Weyl, Methoden der organischen Chemie (Methods of Organic Chemistry), Georg-Thieme Verlag, Stuttgart; Organic Reactions, John Wiley & Sons,. Inc., New York; and in the abovementioned patent applications), in particular under reaction conditions which are known and suitable for the reactions mentioned. In this case, use can also be made of variants which are known per se but which are not mentioned in more detail here.

The starting materials may also be formed, if desired, in situ in such a way that they are not isolated from the reaction mixture, but immediately reacted further to give the compounds of the formula I.

Preferably, the compounds of the formula I are prepared by reacting compounds of the formula II with compounds of the formula III, preferably in the presence of an inert solvent at temperatures between about 0 and 150° C.

Starting materials of the formula II with X—Y=

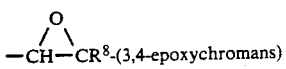

are preferred.

The starting materials III are usually known (compare, for example, DE-OS 3,726,261). If they are not known, they can be prepared by methods which are known per se. Starting materials of the formula II

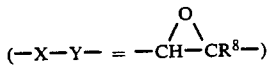

are obtainable by reacting 2-hydroxyacetophenones of the formula 2—HO—$R^6R^7C_6H_2$—$COCH_3$ with ketones of the formula $R^1$—CO—$CH_2R^2$ to give corresponding 4-chromanones of the formula IVa

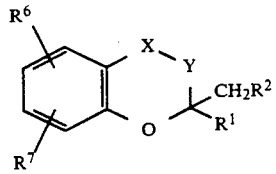

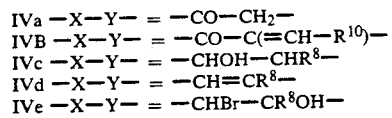

if desired condensing with aldehydes of the formula $R^{10}$—CHO ($R^{10}$=alkyl having 1–5 C atoms) to give 3—alkylidene-4-chromanones of the formula IVb, reducing, for example with $NaBH_4$, to give chromanols of the formula IVc, dehydrating, for example with p-toluenesulfonic acid, to give chromenes of the formula IVd and oxidizing, for example with 3-chloroperbenzoic acid. The last-mentioned oxidation can also be carried out in a number of steps. Thus, for example, the bromohydrins of the formula IVe can initially be prepared using N-bromosuccinimide in aqueous solution and HBr can subsequently be eliminated from these using a base, for example sodium hydroxide solution.

In compounds of the formula II (—X—Y—==—CHE— $CR^3R^8$—), possible "reactively esterified OH groups" are in particular esters with alkylsulfonic acids (in which the alkyl group contains 1–6 C atoms) or with arylsulfonic acids (in which the aryl group contains 6–10 C atoms). These compounds are obtainable from the 4-chromanols of the formula IVc by reacting with an inorganic acid halide such as $PCl_3$, $PBr_3$, $SOCl_2$ or $SOBr_2$ or with a sulfonyl chloride such as methanesulfonyl or p-toluenesulfonyl chloride.

During the reaction of II with III it is expedient to work in the presence of a base. Suitable bases are preferably alkali metal alkyls, in particular methyllithium or butyllithium, alkali metal dialkylamides, in particular lithium diisopropylamide, furthermore, for example, hydroxides, carbonates, alkoxides, hydrides and also amides of alkali metals or alkaline earth metals, such as NaOH, KOH, Ca(OH)$_2$, Na$_2$CO$_3$, K$_2$CO$_3$, Na methoxide or K methoxide, Na ethoxide or K ethoxide or Na tert.butoxide or K tert.-butoxide, NaH, KH, CaH$_2$, NaNH$_2$, KNH$_2$, and in addition organic bases such as triethylamine or pyridine, which can also be used in excess and then at the same time serve as a solvent.

Suitable inert solvents are, in particular, alcohols such as methanol, ethanol, isopropanol, n-butanol or tert.-butanol; ethers such as diethyl ether, diisopropyl ether, tetrahydrofuran (THF) or dioxane; glycol ethers such as ethylene glycol monomethyl ether or ethylene glycol monoethyl ether (methyl glycol or ethyl glycol), ethylene glycol dimethyl ether (diglyme); ketones such as acetone or butanone; nitriles such as acetonitrile; nitro compounds such as nitromethane or nitrobenzene; esters such as ethyl acetate; amides such as dimethylformamide (DMF), dimethylacetamide or hexamethylphosphoramide; sulfoxides such as dimethyl sulfoxide (DMSO); chlorinated hydrocarbons such as dichloromethane, chloroform, trichloroethylene, 1,2-dichloroethane or carbon tetrachloride; hydrocarbons such as benzene, toluene or xylene. Mixtures of these solvents with one another are furthermore suitable.

The epoxide II

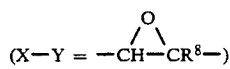

$(X-Y = -CH-CR^8-)$ can also be prepared in situ, for example by the action of a base on the corresponding bromohydrin IVe.

A particularly preferred procedure consists in boiling equivalent amounts of the starting materials of the formulae II and III in an alcohol such as ethanol in the presence of a base such as pyridine for some time.

Compounds of the formula I, in which $R^2$ is OH or NH$_2$, are preferably prepared by treating a compound otherwise corresponding to the formula I, but which, instead of $R^2$, carries a group $-OR^9$ or $-NHR^9$ in which $R^9$ is a protecting group which can be removed by hydrogenolysis or solvolysis, with a hydrogenolyzing or solvolyzing agent.

The starting materials are accessible, for example, by reaction of a compound corresponding to II, but which, instead of $R^2$, carries a group $-OR^9$ or $-NHR^9$, with a compound of the formula III.

Suitable protecting groups $R^9$ are the customary hydroxyl or amino protecting groups, such as are used, for example, in preparative organic chemistry, in particular in peptide chemistry. Some characteristic groups for $R^9$ are benzyl, tetrahydropyran-2-yl, tert.butoxycarbonyl, benzyloxycarbonyl, 2-alkoxyethoxymethyl such as 2-methoxyethoxymethyl ("MEM", which can be removed, for example, with ZnBr$_2$ or TiCl$_4$ in dichloromethane) or 2-trialkylsilylethoxymethyl such as 2-trimethylsilylethoxymethyl ("SEM", which can be removed, for example, with F-ions).

A compound of the formula I in which $R^3$=OH and $R^4$=H can be converted into a compound of the formula I in which $R^3$ and $R^4$ together are a bond by treating with a dehydrating agent. This is carried out, for example by the action of one of the bases mentioned, for example NaOH or NaH, in one of the solvents mentioned, for example THF, dioxane or DMSO, at temperatures between 0° and 150° C.

Furthermore, one or more of the radicals $R^2$, $R^3$, $R^5$, $R^6$ and/or $R^7$ can be converted into other radicals $R^2$, $R^3$, $R^5$, $R^6$ and/or $R^7$ in a compound of the formula I.

For example, it is possible to replace an H atom by a halogen atom by means of a halogenation or by a nitro group by means of a nitration and/or to reduce a nitro group to an amino group and/or to alkylate or acylate an amino or hydroxyl group and/or to convert a cyano group (for example with HCl in water/methanol at 20°-100°) into a carboxyl group or (for example with Raney nickel in water/acetic acid/pyridine in the presence of sodium phosphate) into a formyl group or (for example with KOH in tert.-butanol) into a carbamoyl group or (for example with H$_2$S in pyridine/triethylamine) into a thiocarbamoyl group and/or to dehydrate a carbamoyl group (for example with POCl$_3$) to a cyano group and/or to convert a $-CO-NH-$ group, (for example with P$_2$S$_5$ or with Lawesson reagent in toluene) into a $-CS-NH-$ or $-C(SH)=N$-group.

Nitration is carried out under customary conditions, for example using a mixture of concentrated HNO$_3$ and concentrated H$_2$SO$_4$ at temperatures between 0° and 30° C. If at least one of the substituents $R^6$ and $R^7$ is an electronegative group such as CN or NO$_2$, the nitration predominantly takes place at the radical $R^5$; otherwise mixtures are usually obtained in which the nitro groups are on the radical $R^5$ or on the chroman ring.

This applies analogously to the halogenation which can be carried out, for example, using elemental chlorine or bromine in one of the customary inert solvents at temperatures between about 0° and 30° C.

A primary or secondary amino group and/or an OH group can be converted into the corresponding secondary or tertiary amino group and/or alkoxy group by treating with alkylating agents. Suitable alkylating agents are, for example, compounds of the formulae A—Cl, A—Br or A—I or corresponding sulfuric acid or sulfonic acid esters, such as methyl chloride, bromide or iodide, dimethyl sulfate or methyl p-toluenesulfonate. In addition, for example, one or two methyl groups can be introduced with formaldehyde in the presence of formic acid. The alkylation is preferably carried out in the presence or absence of one of the inert solvents mentioned, for example DMF, at temperatures between about 0° and about 120° C., in which case a catalyst can also be present, preferably a base such as potassium tert.-butoxide or NaH.

Suitable acylating agents for the acylation of amino or hydroxyl groups are preferably the halides (for example chlorides or bromides) or anhydrides of carboxylic acids of the formula Ac—OH, for example acetic anhydride, propionyl chloride, isobutyryl bromide, formic acid/acetic anhydride and benzoyl chloride. The addition of a base such as pyridine or triethylamine during the acylation is possible. The acylation is preferably carried out in the presence or absence of an inert nitrile such as acetonitrile, an amide such as DMF or an excess of a tertiary base such as pyridine or triethylamine, at temperatures between about 0° and about 160° C. preferably between 20° and 120° C. Formylation is also carried out using formic acid in the presence of pyridine.

A base of the formula I can be converted into the respective acid addition salt using an acid. Acids which give physiologically acceptable salts are particularly suitable for this reaction Thus, inorganic acids can be used, for example sulfuric acid, nitric acid, hydrohalic acids such as hydrochloric acid or hydrobromic acid, phosphoric acids such as orthophosphoric acid, sulfamic acid, and in addition organic acids, in particular aliphatic, alicyclic, araliphatic, aromatic or heterocyclic monobasic or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2- or 3-phenylpropionic acid, citric acid, gluconic acid, ascorbic acid, nicotinic acid, isonicotinic acid, methanesulfonic or ethanesulfonic acid, ethanedisulfonic acid, 2-hydroxyethanesulfonic acid, benzenesulfonic acid, p-toluenesulfonic acid, naphthalenemonosulfonic and -disulfonic acids, and laurylsulfuric acid. Salts with physiologically unacceptable acids, for example picrates, can be used for purifying the compounds of the formula I.

The compounds of the formula I may possess one or more chiral centers. They can therefore be obtained during their preparation as racemates or also, if optically active starting materials are used, in optically active form. If the compounds have two or more chiral centers, they may be obtained during synthesis as mixtures of racemates from which the individual racemates can be isolated in pure form, for example by recrystallizing from inert solvents. Thus, for example, compounds of the formula I in which $R^3=OH$ and $R^4=H$ have three chiral centers; during preparation by reaction of II with III, however, very predominantly only two racemates having the trans-position of the $R^5-Z$ group and the substituent $R^3=OH$ are formed. Racemates obtained can, if desired, be separated mechanically, chemically or biochemically into their enantiomers by methods known per se. Thus, diastereomers can be formed from the racemate by reaction with an optically active resolving agent. Suitable resolving agents for basic compounds of the formula I are, for example, optically active acids, such as the D- and L-forms of tartaric acid, dibenzoyltartaric acid, diacetyltartaric acid, camphanic acid, camphorsulfonic acids, mandelic acid, malic acid or lactic acid. Carbinols (I, $R^3=OH$) can in addition be esterified and then resolved with the aid of chiral acylating reagents, for example D- or L-α-methylbenzyl isocyanate (cf. EP-A1-120,428). The different forms of the diastereomers can be separated in a manner known per se, for example by fractional crystallization, and the enantiomers of the formula I can be liberated in a manner known per se from the diastereomers. Resolution of enantiomers is in addition carried out by chromatography on optically active support materials.

The compounds of the formula I and their physiologically acceptable salts can be used for the production of pharmaceutical preparations, in particular in nonchemical ways. In this connection, they can be brought into a suitable form for administration together with at least one solid, liquid and/or semi-liquid excipient or auxiliary and, if desired, in combination with one or more further active compound(s).

The invention in addition relates to agents, in particular pharmaceutical preparations, containing at least one compound of the formula I and/or one of its physiologically acceptable salts.

These preparations can be used as medicaments in human or veterinary medicine. Suitable excipients are organic or inorganic substances which are suitable for enteral (for example oral), parenteral or topical administration and which do not react with the novel compounds, for example water, vegetable oils, benzyl alcohols, polyethylene glycols, glycerol triacetate, gelatin, carbohydrates such as lactose or starch, magnesium stearate, talc, lanolin or petroleum jelly. Tablets, coated tablets, capsules, syrups, elixirs or drops are used in particular for oral administration, suppositories are used in particular for rectal administration, solutions, preferably oily or aqueous solutions, and in addition suspensions, emulsions or implants are used in particular for parenteral administration, and ointments, creams, pastes, lotions, gels, sprays, foams, aerosols, solutions (for example solutions in alcohols such as ethanol or isopropanol, acetonitrile, DMF, dimethylacetamide, 1,2-propanediol or their mixtures with each other and/or with water) or powders are used in particular for topical application. The novel compounds can also be lyophilized and the lyophilizates obtained used, for example, for the production of injection preparations. Liposomal preparations are in particular also suitable for topical application. The preparations mentioned can be sterilized and/or can contain auxiliaries such as lubricants, preservatives, stabilizers and/or wetting agents, emulsifiers, salts for influencing the osmotic pressure, buffer substances, colourants, flavorings and/or aromatizers. They can, if desired, also contain one or more further active compounds, for example one or more vitamins.

The compounds of the formula I and their physiologically acceptable salts can be administered to humans or animals, in particular mammals such as apes, dogs, cats, rats or mice and can be used in the therapeutic treatment of the human or animal body and also in the control of diseases, in particular in the therapy and/or prophylaxis of disturbances of the cardiovascular system, in particular decompensated cardiac insufficiency, angina pectoris, arrhythmia, peripheral or cerebral vessel disorders, and disease conditions which are connected with high blood pressure, and in addition disorders which are connected with changes in the non-vascular musculature, for example asthma or urinary incontinence. All of the compounds of the invention possess all of the foregoing and following utilities, to at least a finite extent.

In this connection, the substances according to the invention are usually administered analogously to known antianginals or hypotensives, for example nicorandil or cromakalim, preferably in doses between about 0.01 and 5 mg, in particular between 0.02 and 0.5 mg per dose unit. The daily dose is preferably between about 0.0001 and 0.1, in particular between 0.0003 and 0.01 mg/kg of body weight. The specific dose for each particular patient dependents, however, on a variety of factors, for example on the efficacy of the specific compound employed, on the age, body weight, the general state of health, sex, on the food, on the time and route of administration, on the excretion rate, medicament combination and severity of the particular disease to which the therapy applies. Oral administration is preferred. One of ordinary skill in the art could clearly determine effective amounts for a given utility based on conventional protocols with only routine experimentation.

The compounds of the formula I and their salts are in addition suitable, in particular on topical application, for the treatment of alopecia areata. For this purpose, in particular, pharmaceutical preparations are used which are suitable for the topical treatment of the scalp and which are mentioned above. They contain about 0.005 to 10, preferably 0.5 to 3, % by weight of at least one compound of the formula I and/or at least one of its salts. Otherwise, these compounds can be used against alopecia in analogy to the statements in WO 88/00822.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, if any, cited above and below, and of corresponding application Federal Republic of Germany P 39 26 001.1, filed August 5, 1989, are hereby incorporated by reference.

In the following examples "customary working up" means:
water is added, if necessary; the mixture is extracted using an organic solvent such as ethyl acetate, the organic phase is separated off, dried over sodium sulfate, filtered and evaporated, and the residue is purified by chromatography and/or crystallization.

EXAMPLES

Example 1

A mixture of 23.1 g of 2-methoxymethyl-2-methyl3,4-epoxy-6-cyanochroman, 9.5 g of 1H-2-pyridone, 12 ml of pyridine and 600 ml of ethanol is boiled for 72 hours. About 300 ml are removed by distillation, the mixture is cooled and filtered, the solution is evaporated and the residue is worked up in the customary manner. 2-Methoxymethyl-2-methyl-4-(1,2-dihydro-2-oxo-1-pyridyl)-6-cyano3-chromanol, stereoisomer mixture ("A") is obtained, which can be separated into isomer "A1" (CH$_3$ and OH in the cis-position; m.p. 216°-218° C.) and isomer "A2" (CH$_3$ and OH in the trans-position; m.p. 210°-212° C.) by chromatography (silica gel; ethyl acetate/methanol).

The starting material is obtained as follows:

a) a mixture of 50 g of 3-acetyl-4-hydroxybenzonitrile, 70 ml of methoxy-2-propanone, 6 ml of pyrrolidine and 300 ml of toluene is boiled in a water separator for 3 hours. The mixture is evaporated, the residue is worked up in the customary manner (ethyl acetate/dil. hydrochloric acid) and 2-methoxymethyl-2-methyl-6-cyano-4-chromanone is obtained, m.p. 79°-81° C.

b) 7 g of NaBH$_4$ are added in portions with stirring to a solution of 31.4 g of the above chromanone in 600 ml of methanol. The mixture is stirred for a further hour and evaporated, the residue is worked up in the customary manner and 2-methoxymethyl-2-methyl-6-cyano-4-chromanol is obtained, stereoisomer mixture, b.p. 160° C./0.133 mbar (air bath temperature, bulb tube).

c) A solution of 13 g of the above chromanol and 0.8 g of p-toluenesulphonic acid in 100 ml of toluene is boiled in a water separator for 3 hours. The mixture is evaporated, the residue is dissolved in dichloromethane, the solution is chromatographed on silica gel using petroleum ether/ether and 2-methoxymethyl-2-methyl-6-cyano-3-chromene is obtained, b.p. 135° C./0.133 mbar (air bath temperature, bulb tube).

d) A solution of 21.1 g of m-chloroperbenzoic acid in 100 ml of dichloromethane is added dropwise with stirring and ice-cooling to a solution of 13 g of the above chromene in 50 ml of dichloromethane. The mixture is stirred at 20° C. for 3.5 hours, a further solution of 5 g of m-chloroperbenzoic acid in 30 ml of dichloromethane being added dropwise after 3 hours, washed with dilute sodium hydroxide solution and worked up further in the customary manner. 2-methoxymethyl-2-methyl-3,4-epoxy6-cyanochroman is obtained as an isomer mixture which can be separated into two isomers (m.p. 88°-90° C. or oil) by chromatography (silica gel; petroleum ether/ether 4:6).

The following are obtained analogously
2-methoxymethyl-2-methyl-3,4-epoxy-6-bromochroman
2-methoxymethyl-2-methyl-3,4-epoxy-6-nitrochroman
2-methoxymethyl-2-methyl-3,4-epoxy-6-methoxycarbonylchroman
2-methoxymethyl-2,3-dimethyl-3,4-epoxy-6-cyanochroman
2-methoxymethyl-2,3-dimethyl-3,4-epoxy-6-bromochroman
2-methoxymethyl-2,3-dimethyl-3,4-epoxy-6-nitrochroman
2-methoxymethyl-2,3-dimethyl-3,4-epoxy-6-methoxycarbonylchroman
2-methoxymethyl-2-methyl-3,4-epoxy-6-carbamoylchroman and, from these epoxides with 1H-2-pyridone, 4-hydroxy-1H-2-pyridone, 3-hydroxy-1,6-dihydro-3-pyridazinone (=3,6-pyridazindiol), 1-methyl-3-hydroxy-1,6-dihydro-3-pyridazinone, 2-pyrrolidinone or 1,3-cyclopentandione:
2-methoxymethyl-2-methyl-4-(1,2-dihydro-2-oxo-1-pyridyl)-6-bromo-3-chromanol
2-methoxymethyl-2-methyl-4-(1,2-dihydro-2-oxo-1-pyridyl)-6-nitro-3-chromanol
2-methoxymethyl-2-methyl-4-(1,2-dihydro-2-oxo-1-pyridyl)-6-methoxycarbonyl-3-chromanol
2-Methoxymethyl-2-methyl-4-(1,2-dihydro-2-oxo-4-pyridyloxy)-6-cyano-3-chromanol
2-Methoxymethyl-2-methyl-4-(1,2-dihydro-2-oxo-4-pyridyloxy)-6-bromo-3-chromanol
2-Methoxymethyl-2-methyl-4-(1,2-dihydro-2-oxo-4-pyridyloxy)-6-nitro-3-chromanol
2-Methoxymethyl-2-methyl-4-(1,2-dihydro-2-oxo-4-pyridyloxy)-6-methoxycarbonyl-3-chromanol
2-Methoxymethyl-2-methyl-4-(1,6-dihydro-6-oxo-3-pyridazinyloxy)-6-cyano-3-chromanol
2-Methoxymethyl-2-methyl-4-(1,6-dihydro-6-oxo-3-pyridazinyloxy)-6-bromo-3-chromanol
2-Methoxymethyl-2-methyl-4-(1,6-dihydro-6-oxo-3-pyridazinyloxy)-6-nitro-3-chromanol
2-Methoxymethyl-2-methyl-4-(1,6-dihydro-6-oxo-3-pyridazinyloxy)-6-methoxycarbonyl-3-chromanol
2-Methoxymethyl-2-methyl-4-(1,6-dihydro-1-methyl-6-oxo-3-pyridazinyloxy)-6-cyano-3-chromanol
2-Methoxymethyl-2-methyl-4-(1,6-dihydro-1-methyl-6-oxo-3-pyridazinyloxy)-6-bromo-3-chromanol
2-Methoxymethyl-2-methyl-4-(1,6-dihydro-1-methyl-6-oxo-3-pyridazinyloxy)-6-nitro-3-chromanol
2-Methoxymethyl-2-methyl-4-(1,6-dihydro-1-methyl-6-oxo-3-pyridazinyloxy)-6-methoxycarbonyl-3-chromanol
2-Methoxymethyl-2-methyl-4-(2-oxopyrrolidino)-6-cyano-3-chromanol
2-Methoxymethyl-2-methyl-4-(2-oxopyrrolidino)-6-bromo-3-chromanol
2-Methoxymethyl-2-methyl-4-(2-oxopyrrolidino)-6-nitro-3-chromanol
2-Methoxymethyl-2-methyl-4-(2-oxopyrrolidino)-6-methoxycarbonyl-3-chromanol
2-Methoxymethyl-2-methyl-4-(3-oxo-1-cyclopentenyloxy)-6-cyano- 3-chromanol 2-Methoxymethyl-2-methyl-4-(3-oxo-1-cyclopentenyloxy)-6-bromo-3-chromanol
2-Methoxymethyl-2-methyl-4-(3-oxo-1-cyclopentenyloxy)-6-nitro-3-chromanol
2-Methoxymethyl-2-methyl-4-(3-oxo-1-cyclopentenyloxy)-6-methoxycarbonyl-3-chromanol
2-Methoxymethyl-2,3-dimethyl-4-(1,2-dihydro-2-oxo-1-pyridyl)-6-cyano-3-chromanol
2-Methoxymethy-2,3-dimethyl-4-(1,2-dihydro-2-oxo-1-pyridyl)-6-bromo-3-chromanol
2-Methexymethyl-2,3-dimethy-4-(1,2-dihydro-2-oxo-1-pyridyl)-6-nitro-3-chromanol
2-Methoxymethyl-2,3-dimethyl-4-(1,2-dihydro-2-oxo-1-pyridyl)-6-methoxycarbonyl-3-chromanol
2-Methoxymethyl-2,3-dimethyl-4-(1,2-dihydro-2-oxo-4-pyridyloxy)-6-cyano-3-chromanol
2-Methoxymethyl-2,3-dimethyl-4-(1,2-dihydro-2-oxo-4-pyridyloxy)-6-bromo-3-chromanol
2-Methoxymethyl-2,3-dimethyl-4-(1,2-dihydro-2-oxo-4-pyridyloxy)-6-nitro-3-chromanol
2-Methoxymethyl-2,3-dimethyl-4-(1,2-dihydro-2-oxo-4-pyridyloxy)-6-methoxycarbonyl-3-chromanol
2-Methoxymethyl-2,3-dimethyl-4-(1,6-dihydro-6-oxo-3-pyridazinyloxy)-6-cyano-3-chromanol
2-Methoxymethyl-2,3-dimethyl-4-(1,6-dihydro-6-oxo-3-pyridazinyloxy)-6-bromo-3-chromanol
2-Methoxymethyl-2,3-dimethyl-4-(1,6-dihydro-6-oxo-3-pyridazinyloxy)-6-nitro-3-chromanol
2-Methoxymethyl-2,3-dimethyl-4-(1,6-dihydro-6-oxo-3-pyridazinyloxy)-6-methoxycarbonyl-3-chromanol
2-Methoxymethyl-2,3-dimethyl-4-(1,6-dihydro-1-methyl-6oxo-3-pyridazinyloxy)-6-cyano-3-chromanol
2-Methoxymethyl-2,3-dimethyl-4-(1,6-dihydro-1-methyl-6-oxo-3-pyridazinyloxy)-6-bromo-3-chromanol
2-Methoxymethyl-2,3-dimethyl-4-(1,6-dihydro-1-methyl-6-oxo-3-pyridazinyloxy)-6-nitro-3-chromanol
2-Methoxymethyl-2,3-dimethyl-4-(1,6-dihydro-1-methyl-6-oxo-3-pyridazinyloxy)-6-methoxycarbonyl-3-chromanol
2-Methoxymethyl-2,3-dimethyl-4-(2-oxopyrrolidino)-6-cyano-3-chromanol
2-Methoxymethyl-2,3-dimethyl-4-(2-oxopyrrolidino)-6-bromo-3-chromanol
2-Methoxymethyl-2,3-dimethyl-4-(2-oxopyrrolidino)-6-nitro-3-chromanol
2-Methoxymethyl-2,3-dimethyl-4-(2-oxopyrrolidino)-6-methoxycarbonyl-3-chromanol
2-Methoxymethyl-2,3-dimethyl-4-(3-oxo-1-cyclopentenyloxy)-6-cyano-3-chromanol
2-Methoxymethyl-2,3-dimethyl-4-(3-oxo-1-cyclopentenyloxy)-6-bromo-3-chromanol
2-Methoxymethyl-2,3-dimethyl-4-(3-oxo-1-cyclopentenyloxy)-6-nitro-3-chromanol
2-Methoxymethyl-2,3-dimethyl-4-(3-oxo-1-cyclopentenyloxy)-6-methoxycarbonyl-3-chromanol
2-Methoxymethyl-2-methyl-4-(1,2-dihydro-2-oxo-1-pyridyl)6-carbamoyl-3-chromanol.

Example 2

1.2 g of 80% NaH are added to a solution of 2.96 g of 2-methoxymethyl-2-methyl-4-bromo-6-cyanochroman (stereoisomer mixture; obtainable from 2-methoxymethyl-2-methyl-6-cyano-4-chromanol and PBr₃ in toluene at 20° C.) and 2 g of 1H-2-pyridone in 70 ml of DMSO and the mixture is stirred at 20° for 3 days. Customary working up gives 2-methoxymethyl-2-methyl-4-(1,2-dihydro-2-oxo-1-pyridyl)-6-cyano-chroman, isomer mixture.

Example 3

A mixture of 10 g of "A", 3 g of NaOH and 350 ml of dioxane is boiled for 20 min. The mixture is cooled, filtered, the filtrate is evaporated and 2-methoxymethyl2-methyl-4-(1,2-dihydro-2-oxo-1-pyridyl)-6-cyano-3chromene ("B") is obtained, m.p. 160°-162° C.

The following are obtained analogously by dehydration of the corresponding 3-chromanols:
2-Methoxymethyl-2-methyl-4-(1,2-dihydro-2-oxo-1-pyridyl)-6-bromo-3-chromene
2-Methoxymethyl-2-methyl-4-(1,2-dihydro-2-oxo-1-pyridyl)6-nitro-3-chromene
2-Methoxymethyl-2-methyl-4-(1,2-dihydro-2-oxo-1-pyridyl)-6-methoxycarbonyl-3-chromene
2-Methoxymethyl-2-methyl-4-(1,2-dihydro-2-oxo-4-pyridyl-oxy)-6-cyano-3-chromene
2-Methoxymethyl-2-methyl-4-(1,2-dihydro-2-oxo-4-pyridyloxy)-6-bromo-3-chromene
2-Methoxymethyl-2-methyl-4-(1,2-dihydro-2-oxo-4-pyridyloxy)-6-nitro-3-chromene
2-Methoxymethyl-2-methyl-4-(1,2-dihydro-2-oxo-4-pyridyloxy)-6-methoxycarbonyl-3-chromene
2-Methoxymethyl-2-methyl-4-(1,6-dihydro-6-oxo-3-pyridazinyloxy)-6-cyano-3-chromene
2-Methoxymethyl-2-methyl-4-(1,6-dihydro-6-oxo-3-pyridazinyloxy)-6-bromo-3-chromene
2-Methoxymethyl-2-methyl-4-(1,6-dihydro-6-oxo-3-pyridazinyloxy)-6-nitro-3-chromene
2-Methoxymethyl-2-methyl-4-(1,6-dihydro-6-oxo-3-pyridazinyloxy)-6-methoxycarbonyl-3-chromene
2-Methoxymethyl-2-methyl-4-(1,6-dihydro-1-methyl-6-oxo-3-pyridazinyloxy)-6-cyano-3-chromene
2-Methoxymethyl-2-methyl-4-(1,6-dihydro-1-methyl-6-oxo- 3-pyridazinyloxy)-6-bromo-3-chromene
2-Methoxymethyl-2-methyl-4-(1,6-dihydro-1-methyl-6-oxo-3-pyridazinyloxy)-6-nitro-3-chromene
2-Methoxymethyl-2-methyl-4-(1,6-dihydro-1-methyl-6-oxo-3-pyridazinyloxy)-6-methoxycarbonyl-3-chromene
2-Methoxymethyl-2-methyl-4-(2-oxopyrrolidino)-6-cyano-3-chromene
2-Methoxymethyl-2-methyl-4-(2-oxopyrrolidino)-6-bromo-3-chromene
2-Methoxymethyl-2-methyl-4-(2-oxopyrrolidino)-6-nitro-3-chromene
2-Methoxymethyl-2-methyl-4-(2-oxopyrrolidino)-6-methoxycarbonyl-3-chromene
2-Methoxymethyl-2-methyl-4-(3-oxo-1-cyclopentenyloxy)-6-cyano-3-chromene
2-Methoxymethyl-2-methyl-4-(3-oxo-1-cyclopentenyloxy)-6-bromo-3-chromene
2-Methoxymethyl-2-methyl-4-(3-oxo-1-cyclopentenyloxy)-6-nitro-3-chromene
2-Methoxymethyl-2-methyl-4-(3-oxo-1-cyclopentenyloxy)-6-methoxycarbonyl-3-chromene
2-Methoxymethyl-2,3-dimethyl-4-(1,2-dihydro-2-oxo-1-pyridyl)-6-cyano-3-chromene
2-Methoxymethyl-2,3-dimethyl-4-(1,2-dihydro-2-oxo-1-pyridyl)-6-bromo-3-chromene
2-Methoxymethyl-2,3-dimethyl-4-(1,2-dihydro-2-oxo-1-pyridyl)-6-nitro-3-chromene
2-Methoxymethyl-2,3-dimethyl-4-(1,2-dihydro-2-oxo-1-pyridyl)-6-methoxycarbonyl-3-chromene
2-Methoxymethyl-2,3-dimethyl-4-(1,2-dihydro-2-oxo-4-pyridyloxy)-6-cyano-3-chromene
2-Methoxymethyl-2,3-dimethyl-4-(1,2-dihydro-2-oxo-4-pyridyloxy)-6-bromo-3-chromene 2-Methoxymethyl-2,3-dimethyl-4-(1,2-dihydro-2-oxo-4-pyridyloxy)-6-nitro-3-chromene
2-Methoxymethyl-2,3-dimethyl-4-(1,2-dihydro-2-oxo-4-pyridyloxy)-6-methoxycarbonyl-3-chromene
2-Methoxymethyl-2,3-dimethyl-4-(1,6-dihydro-6-oxo-3-pyridazinyloxy)-6-cyano-3-chromene
2-Methoxymethyl-2,3-dimethyl-4-(1,6-dihydro-6-oxo-3-pyridazinyloxy)-6-bromo-3-chromene
2-Methoxymethyl-2,3-dimethyl-4-(1,6-dihydro-6-oxo-3-pyridazinyloxy)-6-nitro-3-chromene
2-Methoxymethyl-2,3-dimethyl-4-(1,6-dihydro-6-oxo-3-pyridazinyloxy)-6-methoxycarbonyl-3-chromene
2-Methoxymethyl-2,3-dimethyl-4-(1,6-dihydro-1-methyl-6-oxo-3-pyridazinyloxy)-6-cyano-3-chromene
2-Methoxymethyl-2,3-dimethyl-4-(1,6-dihydro-1-methyl-6-oxo-3-pyridazinyloxy)-6-bromo-3-chromene
2-Methoxymethyl-2,3-dimethyl-4-(1,6-dihydro-1-methyl-6-oxo-3-pyridazinyloxy)-6-nitro-3-chromene
2-Methoxymethyl-2,3-dimethyl-4-(1,6-dihydro-1-methyl-6-oxo-3-pyridazinyloxy)-6-methoxycarbonyl-3-chromene
2-Methoxymethyl-2,3-dimethyl-4-(2-oxopyrrolidino)-6-cyano-3-chromene
2-Methoxymethyl-2,3-dimethyl-4-(2-oxopyrrolidino)-6-bromo-3-chromene
2-Methoxymethyl-2,3-dimethyl-4-(2-oxopyrrolidino)-6-nitro-3-chromene
2-Methoxymethyl-2,3-dimethyl-4-(2-oxopyrrolidino)-6-methoxycarbonyl-3-chromene
2-Methoxymethyl-2,3-dimethyl-4-(3-oxo-1-cyclopentenyloxy)-6-cyano-3-chromene
2-Methoxymethyl-2,3-dimethyl-4-(3-oxo-1-cyclopentenyloxy)-6-bromo-3-chromene
2-Methoxymethyl-2,3-dimethyl-4-(3-oxo-1-cyclopentenyloxy)- 6-nitro-3-chromene
2-Methoxymethyl-2,3-dimethyl-4-(3-oxo-1-cyclopentenyloxy)-6-methoxycarbonyl-3-chromene
2-Methoxymethyl-2-methyl-4-(1,2-dihydro-2-oxo-1-pyridyl)-6-carbamoyl-3-chromene.

Example 4

A mixture of 1 g of 2-methyl-2-(2-tetrahydropyranyloxymethyl)-4-(1,2-dihydro-2-oxo-1-pyridyl)-6-cyano-3-chroman [obtainable from 1-(2-tetrahydropyranyl)2-propanone via 2-methyl-2-(2-tetrahydropyranyloxymethyl)-6-cyano-4-chromanone, 2-methyl-2-(2-tetrahydropyranyloxymethyl)-6-cyano-4-chromanol, 2-methyl-2-(2-tetrahydropyranyloxymethyl)-6-cyano-3-chromene and the corresponding 3,4-epoxide] and 15 ml of 10% methanolic HCl solution is boiled for 15 min. Cooling and customary working up gives 2-hydroxymethyl-2-methyl-4-(1,2-dihydro2-oxo-1-pyridyl)-6-cyano-3-chromene. Example 5

A solution of 1 g of 2-benzyloxycarbonylaminomethyl-2-methyl-4-(1,2-dihydro-2-oxo-1-pyridyl)-6-cyano3-chromene [obtainable from 1-benzyloxycarbonylamino-2-propanone ("1-CBZ-2-propanone") via 2-CBZ-aminomethyl-2-methyl-6-cyano-4-chromanone, the corresponding 4-chromanol, the corresponding 3-chromene and the corresponding 3,4-epoxide] in 20 ml of dioxane is hydrogenated on 0.5 g of 5% Pd-carbon at 20° C. and 1 bar until the calculated amount of H₂ has been absorbed. The mixture is filtered, the solution is evaporated and 2-aminomethyl-2-methyl-4-(1,2-dihydro-2-oxo-1-pyridyl)-6-cyano-3-chromene is obtained.

Example 6

A mixture of 2 g of "A", 11.7 ml of formic acid and 3.3 ml of acetic anhydride is allowed to stand at 20° C. for 16 hours and subsequently warmed to 40° C. for 1 hour. Evaporation and customary working up gives 2-methoxymethyl-2-methyl-3-formyloxy-4-(1,2-dihydro-2-oxo-1-pyridyl)-6-cyanochroman, an isomer mixture which can be separated by chromatography.

Example 7

A mixture of 1 g of "A" and 5 ml of acetic anhydride is boiled for 1 hour. The mixture is cooled, worked up in the customary manner and 2-methoxymethyl-2-methyl-3-acetoxy-4-(1,2-dihydro-2-oxo-1-pyridyl)-6-cyanochroman, an isomer mixture which can be separated by chromatography, is obtained.

Example 8

A solution of 1 g of 2-methoxymethyl-2-methyl-4-(1,2-dihydro-2-oxo-1-pyridyl)-6-nitro-3-chromanol in 25 ml of methanol is hydrogenated at 20° C. and 1 bar on 0.5 g of 5% Pd-C until hydrogenation stops. The mixture is filtered, the filtrate is evaporated and 2-methoxymethyl-2-methyl-4-(1,2-dihydro-2-oxo-1-pyridyl)-6-amino3-chromanol, an isomer mixture which can be separated by chromatography, is obtained.

Example 9

A solution of 4 g of 2-methoxymethyl-2-methyl-4-(1,2-dihydro-2-oxo-1-pyridyl)-6-carbamoyl-3-chromene is hydrogenated on 4 g of 20% Pd-C at 20° C. and 1 bar in 200 ml of methanol, the mixture is filtered, the filtrate is evaporated and 2-methoxymethyl-2-methyl-4-(1,2-dihydro-2-oxo-1-pyridyl)-6-carbamoylchroman is obtained, m.p. 177°-179° C.

Example 10

A solution of 1 g of 2-methoxymethyl-2-methyl-4-(1,2-dihydro-2-oxo-1-pyridyl)-6-amino-3-chromanol in 15 ml of formic acid and 1 ml of pyridine is boiled for 24 hours and evaporated. Customary working up gives 2-methoxymethyl-2-methyl-4-(1,2-dihydro-2-oxo-1-pyridyl)-6-formamido-3-chromanol.

Example 11

A mixture of 1 g of 2-methoxymethyl-2-methyl-4-(1,2-dihydro-2-oxo-1-pyridyl)-6-amino-3-chromanol, 10 ml of acetic anhydride and 10 ml of pyridine is allowed to stand at 20° C. for 24 hours. The mixture is evaporated, worked up in the customary manner and 2-methoxymethyl-2-methyl-4-(1,2-dihydro-2-oxo-1-pyridyl)-6-acetamido-3-chromanol is obtained.

Example 12

HCl is passed into a boiling solution of 1 g of "B" in 50 ml of methanol and 2 ml of water with stirring for 12 hours. The mixture is allowed to cool and to stand overnight. The precipitated 2-methoxymethyl-2-methyl-4-(1,2-dihydro-2-oxo-1-pyridyl)-3-chromene-6-carboxylic acid is filtered off.

Example 13

A mixture of 2.98 g of 2-methoxymethyl-2-methyl-4-(1,2-dihydro-2-oxo-1-pyridyl)-6-carbamoylchroman, 2 ml of POCl₃ and 200 ml of 1,2-dichloroethane is boiled for 45 min. Cooling and customary working up gives 2-methoxymethyl-2-methyl-4-(1,2-dihydro-2-oxo-1-pyridyl)-6-cyanochroman.

Example 14

A mixture of 1 g of "B", 10 g of trisodium phosphate dodecahydrate, 9 ml of pyridine, 9 ml of water, 22 ml of acetic acid and 8 g of Raney nickel (watermoist) is stirred at 20° C. for 3 hours. The mixture is filtered, the filtrate is worked up in the customary manner and 2-methoxymethyl-2-methyl-4-(1,2-dihydro-2-oxo-1-pyridyl)-6-formyl-3-chromene is obtained.

Example 15

H₂S is passed into a solution of 1 g of "B" in a mixture of 7 ml of pyridine and 7 ml of triethylamine at 20° C. for 3 hours, the mixture is evaporated, the residue is worked up in the customary manner and 2-methoxymethyl2-methyl-4-(1,2-dihydro-2-oxo-1-pyridyl)-6-thiocarbamoyl3-chromene is obtained.

Example 16

A solution of 280 mg of 2-methoxymethyl-2-methyl-4-(1,2-dihydro-2-oxo-1-pyridyl)-6-bromo-3-chromanol is hydrogenated on 140 mg of 20% Pd-C in 80 ml of methanol at 20° and 1 bar, the mixture is filtered, the filtrate is evaporated and 2-methoxymethyl-2-methyl-4-(1,2-dihydro-2-oxo-1-pyridyl)-3-chromanol m.p. 244°-246° C. is obtained after chromatographic purification on silica gel.

The examples below relate to pharmaceutical preparations which contain compounds of the formula I and/or their physiologically acceptable salts.

Example 1

Tablets

A mixture of 0.2 kg of "B", 136.3 kg of calcium hydrogenphosphate, 15 kg of cornflour, 10 kg of microcrystalline cellulose, 5.5 kg of insoluble polyvinylpyrrolidone (PVP), 1.5 kg of highly disperse silica and 1.5 kg of magnesium stearate is compressed to give tablets in a customary manner. Each 170 mg tablet contains 0.2 mg of active compound.

Example 2

Coated tablets

Tablets are pressed analogously to Example 1, but without the addition of PVP, and are subsequently coated in a customary manner with a coating of sucrose, cornflour, talc, tragacanth and colorant.

Example 3

Lacquered tablets

Tablet cores (170 mg), which are subsequently lacquered in a customary manner so that each lacquered tablet is coated with 3.922 mg of a lacquer which comprises 2.2 mg of hydroxypropylmethylcellulose, 0.53 mg of polyethylene glycol 400, 0.85 mg of titanium dioxide, 0.12 mg of iron(III) oxide (yellow), 0.002 mg of iron(III) oxide (red) and 0.22 mg of silicone oil, are pressed from 0.2 kg of "B", 151.3 kg of lactose, 10 kg of microcrystalline cellulose, 5.5 kg of insoluble PVP, 1.5 kg of highly disperse silica and 1.5 kg of calcium stearate.

Example 4

Capsules

Granules are prepared from 10 g of "A1", 27.5 kg of lactose, 0.35 kg of hydroxypropylmethylcellulose and 0.7 kg of cornflour, these are mixed with 0.15 kg of highly disperse silica and 0.3 kg of magnesium stearate and the mixture is poured into hard gelatin capsules in a customary manner so that each capsule contains 0.1 mg of active compound.

Example 5

Ampoules

A solution of 10 g of "A2" in 70 l of 1,2-propanediol is made up to 100 l with double-distilled water, sterile filtered, and the solution is filled into 1 ml ampoules which are then sealed in a sterile manner. Each ampoule contains 0 1 mg of active compound.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A chroman derivative of formula I

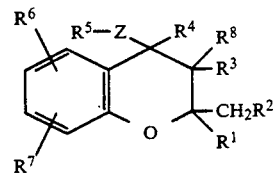

wherein
R¹ is A,
R² is OA,
R³ is OH,
R⁴ is H, or
R³ and R⁴ together are a bond,
R⁵ is a or 2-oxo-1,2-dihydro-1-pyridyl or 2-oxo-2,3-dihydro-4pyridyl radical which is optionally monosubstituted by A,
R⁶ is CN,
R⁷ and R⁸ are each H,
Z is O, NH or a bond, and
A is alkyl having 1-6 C atoms,
or a physiologically acceptable salt thereof.

2. A chroman derivative of claim 1, wherein R¹ is CH₃.

3. A chroman derivative of claim 1, wherein R¹ is CH₃ and R² is OCH₃.

4. A chroman derivative of claim 1, wherein R⁵-Z is 1,2-dihydro-2-oxo-1-pyridyl, 2-hydroxy-4-pyridyloxy 5. A chroman derivative of claim 1, wherein R⁵-Z is 1,2-dihydro-2-oxo-1-pyridyl.

6. A chroman derivative of claim 1, wherein
R¹ is CH₃,
R² is OCH₃, and
R⁵—Z is 1,2-dihydro-2-oxo-1-pyridyl or 2-hydroxy-4pyridyloxy.

7. A chroman derivative of claim 1, wherein $R^1$ is $CH_3$,
$R^2$ is $OCH_3$,
$R^5$-Z is 1,2-dihydro-2-oxo-1-pyridyl.

8. a) 2-methoxymethyl-2-methyl-4-(1,2-dihydro-2-oxo-1-pyridyl)-6-cyano-3-chromanol; or b) 2-methoxymethyl-2-methyl-4-(1,2-dihydro-2-oxo-1-pyridyl)-6-cyano-3-chromene, each a compound of claim 1.

9. A pharmaceutical composition comprising an effective amount of a compound of claim 1 and a pharmaceutically acceptable carrier.

10. A method of treating decompensated cardiac insufficiency, angina pectoris, cardiac arrhythmia, a peripheral or cerebral vessel disorder or hypertension in a host in need of such treatment comprising administering to said host an effective amount of a compound of claim 1.

* * * * *

UNITED STATES PATENT AND TRADEMARK OFFICE
CERTIFICATE OF CORRECTION

PATENT NO. : 5,130,322
DATED : July 14, 1992
INVENTOR(S) : Rolf Gericke et al

It is certified that error appears in the above-indentified patent and that said Letters Patent is hereby corrected as shown below:

Col. 18, line 47, claim 1, after a -- delete (or) --.

Col. 18, line 67, claim 6, insert "-" after 4

Col. 19, line 3, claim 7, After pyridyl, -- insert " or 2-hydroxy-4-pyridyloxy".

Signed and Sealed this

Fourteenth Day of September, 1993

Attest:

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO. : 5,130,322
DATED : July 14, 1992
INVENTOR(S) : Rolf GERICKE et al.

It is certified that error appears in the above-indentified patent and that said Letters Patent is hereby corrected as shown below:

Claim 1; Col. 18; Line 48: After 4 insert (a hyphen).

Claim 4; Col. 18; Line 60: after pyridyloxy insert --.--
Claim 6; Col. 18; Line 67: after 4 insert -- - --.
Claim 8; Col. 19; Line 4: Move "8. a)" down one line.

This certificate supercedes Certificate of Correction issued September 14, 1993.

Signed and Sealed this

Twenty-third Day of August, 1994

Attest:

BRUCE LEHMAN

Attesting Officer

Commissioner of Patents and Trademarks